(12) United States Patent
Lucas et al.

(10) Patent No.: US 7,344,843 B2
(45) Date of Patent: Mar. 18, 2008

(54) AGONISTS AND ANTAGONISTS OF PROLIXIN FOR THE TREATMENT OF METABOLIC DISORDERS

(75) Inventors: John Lucas, Concord, MA (US); Deno Dialynas, San Diego, CA (US); Kristen Briggs, Del Mar, CA (US)

(73) Assignee: Serono Genetics Institute S.A., Evry (FR)

( * ) Notice: Subject to any disclaimer, the term of this patent is extended or adjusted under 35 U.S.C. 154(b) by 429 days.

(21) Appl. No.: 10/496,757

(22) PCT Filed: Oct. 14, 2002

(86) PCT No.: PCT/IB02/04668

§ 371 (c)(1),
(2), (4) Date: Oct. 20, 2004

(87) PCT Pub. No.: WO03/045422

PCT Pub. Date: Jun. 5, 2003

(65) Prior Publication Data

US 2005/0069971 A1    Mar. 31, 2005

Related U.S. Application Data

(60) Provisional application No. 60/334,357, filed on Nov. 29, 2001.

(51) Int. Cl.
*G01N 33/53* (2006.01)
(52) U.S. Cl. .......................... 435/7.1; 530/350
(58) Field of Classification Search ............... None
See application file for complete search history.

(56) References Cited

U.S. PATENT DOCUMENTS

| | | | |
|---|---|---|---|
| 6,344,441 B1 | 2/2002 | Bihain et al. | |
| 6,461,821 B1 | 10/2002 | Matsuzawa et al. | |
| 6,566,332 B2 | 5/2003 | Fruebis et al. | |
| 6,579,852 B2 | 6/2003 | Fruebis et al. | |
| 6,867,189 B2 | 3/2005 | Lucas et al. | |
| 6,946,444 B2 | 9/2005 | Bihain et al. | |
| 6,967,091 B2 | 11/2005 | Fruebis et al. | |
| 6,989,367 B2 | 1/2006 | Fruebis et al. | |
| 2002/0151498 A1 | 10/2002 | Bihain et al. | |
| 2003/0092164 A1* | 5/2003 | Gross et al. | ............. 435/252.3 |
| 2003/0215836 A1 | 11/2003 | Young et al. | |
| 2003/0224501 A1 | 12/2003 | Young et al. | |
| 2005/0003997 A1 | 1/2005 | Lucas et al. | |
| 2005/0054565 A1 | 3/2005 | Lucas et al. | |
| 2006/0089311 A1 | 4/2006 | Dialynas et al. | |

FOREIGN PATENT DOCUMENTS

| | | |
|---|---|---|
| EP | 1033134 | 9/2000 |
| WO | WO 99/59618 A1 | 11/1999 |
| WO | WO 00/68380 A2 | 11/2000 |
| WO | WO 00/73448 A1 | 12/2000 |
| WO | WO 01/51645 A1 | 7/2001 |
| WO | WO 02/38766 A2 | 5/2002 |

OTHER PUBLICATIONS

Thompson, J.S. et al., "BAFF-R, a Newly Identified TNF Receptor That Specifically Interacts with BAFF" *Science*, Sep. 14, 2001, pp. 2108-2111, vol. 293, No. 5537.

Yan, M. et al. "Identification of a novel receptor for B lymphocyte stimulator that is mutated in a mouse strain with severe B cell deficiency" *Current Biology*, Oct. 2, 2001, pp. 1547-1552, vol. 11, No. 19.

U.S. Appl. No. 11/132,814, filed May 19, 2005, claims only.

\* cited by examiner

*Primary Examiner*—Robert S. Landsman
*Assistant Examiner*—Gyan Chandra
(74) *Attorney, Agent, or Firm*—Saliwanchik, Lloyd & Saliwanchik

(57) ABSTRACT

The present invention relates to the field of metabolic research, in particular the discovery of compounds effective for reducing body mass and useful for treating obesity-related diseases and disorders. The obesity-related diseases or disorders envisioned to be treated by the methods of the invention include, but are not limited to, hyperlipidemia, atherosclerosis, insulin resistance, diabetes, and hypertension. In particular, the invention provides for methods of identifying and using AGONISTS and ANTAGONISTS of PROLIXIN activity, wherein said activity is selected from the group consisting of lipid partitioning, lipid metabolism, and insulin-like activity.

5 Claims, No Drawings

SEQUENCE LISTING

<160> NUMBER OF SEQ ID NOS: 2

<210> SEQ ID NO 1
<211> LENGTH: 899
<212> TYPE: DNA
<213> ORGANISM: Homo sapiens
<220> FEATURE:
<221> NAME/KEY: CDS
<222> LOCATION: (6)...(560)

<400> SEQUENCE: 1

```
gcacc atg agg cga ggg ccc cgg agc ctg cgg ggc agg gac gcg cca gcc      50
      Met Arg Arg Gly Pro Arg Ser Leu Arg Gly Arg Asp Ala Pro Ala
      1               5                   10                  15 ccc acg ccc tgc gtc ccg gcc gag tgc ttc gac ctg ctg gtc cgc cac        98
Pro Thr Pro Cys Val Pro Ala Glu Cys Phe Asp Leu Leu Val Arg His
                20                  25                  30 tgc gtg gcc tgc ggg ctc ctg cgc acg ccg cgg ccg aaa ccg gcc ggg        146
Cys Val Ala Cys Gly Leu Leu Arg Thr Pro Arg Pro Lys Pro Ala Gly
            35                  40                  45 gcc agc agc cct gcg ccc agg acg gcg ctg cag ccg cag gag tcg gtg        194
Ala Ser Ser Pro Ala Pro Arg Thr Ala Leu Gln Pro Gln Glu Ser Val
        50                  55                  60 ggc gcg ggg gcc ggc gag gcg gcg ctg ccc ctg ccc ggg ctg ctc ttt        242
Gly Ala Gly Ala Gly Glu Ala Ala Leu Pro Leu Pro Gly Leu Leu Phe
    65                  70                  75 ggc gcc ccc gcg ctg ctg ggc ctg gca ctg gcg ctg gtc ctg        290
Gly Ala Pro Ala Leu Leu Gly Leu Ala Leu Ala Leu Val Leu
80                  85                  90                  95 gtg ggt ctg gtg agc tgg agg cgg cga cag cgg cgg ctt cgc ggc gcg        338
Val Gly Leu Val Ser Trp Arg Arg Arg Gln Arg Arg Leu Arg Gly Ala
```

-continued

```
                  100                 105                 110
tcc tcc gca gag gcc ccc gac gga gac aag gac gcc cca gag ccc ctg      386
Ser Ser Ala Glu Ala Pro Asp Gly Asp Lys Asp Ala Pro Glu Pro Leu
            115                 120                 125 gac aag gtc atc att ctg tct ccg gga atc tct gat gcc aca gct cct      434
Asp Lys Val Ile Ile Leu Ser Pro Gly Ile Ser Asp Ala Thr Ala Pro
        130                 135                 140 gcc tgg cct cct cct ggg gaa gac cca gga acc acc cca cct ggc cac      482
Ala Trp Pro Pro Pro Gly Glu Asp Pro Gly Thr Thr Pro Pro Gly His
    145                 150                 155 agt gtc cct gtg cca gcc aca gag ctg ggc tcc act gaa ctg gtg acc      530
Ser Val Pro Val Pro Ala Thr Glu Leu Gly Ser Thr Glu Leu Val Thr
160                 165                 170                 175 acc aag acg gcc ggc cct gag caa caa tag cagggagccg gcaggaggtg        580
Thr Lys Thr Ala Gly Pro Glu Gln Gln  *
                180 gcccctgccc tccctctgga cccccagcca ggggcttgga aatcaaattc agctcttcac    640 tccagcatgc acatgccctc tttctgggac caggctaacc ctgcagaagc acagacacta   700 cagaccacag cattcagccc ccatggagtt tggtgtgctt gcctttggct tcagacctca   760 ccatctttga cagcccttga aggtggtagc ccagctcctg ttcctgtgcc ttcaaaaggc   820 tggggcacta tgagtaaaag accgctttta aatggggaa ggcaccatta agccaaaatg    880 aatctgaaaa aagacaaaa                                                899
```

<210> SEQ ID NO 2
<211> LENGTH: 184
<212> TYPE: PRT
<213> ORGANISM: Homo sapiens

<400> SEQUENCE: 2

```
Met Arg Arg Gly Pro Arg Ser Leu Arg Gly Arg Asp Ala Pro Ala Pro
 1               5                  10                  15

Thr Pro Cys Val Pro Ala Glu Cys Phe Asp Leu Leu Val Arg His Cys
                20                  25                  30

Val Ala Cys Gly Leu Leu Arg Thr Pro Arg Pro Lys Pro Ala Gly Ala
            35                  40                  45

Ser Ser Pro Ala Pro Arg Thr Ala Leu Gln Pro Gln Glu Ser Val Gly
        50                  55                  60

Ala Gly Ala Gly Glu Ala Ala Leu Pro Leu Pro Gly Leu Leu Phe Gly
65                  70                  75                  80

Ala Pro Ala Leu Leu Gly Leu Ala Leu Val Leu Ala Leu Val Leu Val
                85                  90                  95

Gly Leu Val Ser Trp Arg Arg Gln Arg Arg Leu Arg Gly Ala Ser
                100                 105                 110

Ser Ala Glu Ala Pro Asp Gly Asp Lys Asp Ala Pro Glu Pro Leu Asp
            115                 120                 125

Lys Val Ile Ile Leu Ser Pro Gly Ile Ser Asp Ala Thr Ala Pro Ala
        130                 135                 140

Trp Pro Pro Pro Gly Glu Asp Pro Gly Thr Thr Pro Pro Gly His Ser
145                 150                 155                 160

Val Pro Val Pro Ala Thr Glu Leu Gly Ser Thr Glu Leu Val Thr Thr
                165                 170                 175

Lys Thr Ala Gly Pro Glu Gln Gln
            180
```

AGONISTS AND ANTAGONISTS OF PROLIXIN FOR THE TREATMENT OF METABOLIC DISORDERS

CROSS-REFERENCE TO RELATED APPLICATION

This application is the U.S. national stage application of International Patent Application No. PCT/IB02/04668, filed Oct. 14, 2002, which claims the benefit of U.S. Provisional Patent Application No. 60/334,357, filed Nov. 29, 2001.

FIELD OF THE INVENTION

The present invention relates to the field of metabolic research, in particular the discovery of compounds effective for reducing body mass and maintaining weight loss and useful for treating obesity-related diseases and disorders. The obesity-related diseases or disorders envisioned to be treated by the methods of the invention include, but are not limited to, hyperlipidemia, atherosclerosis, insulin resistance, diabetes, and hypertension. The present invention additionally relates elsewhere to the field of metabolic research, in particular the discovery of compounds effective for increasing body mass and useful for treating disorders associated with excessive weight loss. Applicant reserves the right to exclude any of the aforesaid obesity-related diseases or disorders. The disorders associated with excessive weight loss and envisioned to be treated by the methods of the invention include, but are not limited to, cachexia, cancer-related weight loss, AIDS-related weight loss, chronic inflammatory disease-related weight loss, and anorexia. Applicant reserves the right to exclude any of the aforesaid disorders associated with excessive weight loss.

In particular, the invention provides for methods of identifying and using AGONISTS and ANTAGONISTS of PROLIXIN activity, wherein said activity is selected from the group consisting t of lipid partitioning, lipid metabolism, and insulin-like activity.

BACKGROUND OF THE INVENTION

The following discussion is intended to facilitate the understanding of the invention, but is not intended nor admitted to be prior art to the invention.

Obesity is a public health problem that is serious, widespread, and increasing. In the United States, 20 percent of the population is obese; in Europe, a slightly lower percentage is obese (Friedman (2000) Nature 404:632-634). Obesity is associated with increased risk of hypertension, cardiovascular disease, diabetes, and cancer as well as respiratory complications and osteoarthritis (Kopelman (2000) Nature 404:635-643). Even modest weight loss ameliorates these associated conditions.

Recently it was shown that particular carboxyl-terminal fragments of the full-length ACRP30 (mouse) and APM1 (human) polypeptides have unexpected effects in vitro and in vivo, including utility for weight reduction, prevention of weight gain, and control of blood glucose levels (Fruebis et al (2001) Proc Natl Acad Sci USA 98:2005-10). The effects of ACRP30 fragment administration in mammals also include reduction of elevated free fatty acid levels including elevated free fatty acid levels caused by administration of epinephrine, i.v. injection of "intralipid", or administration of a high fat test meal, as well as increased fatty acid oxidation in muscle cells, and weight reduction in mammals consuming a normal or high fat/high sucrose diet.

Throughout this application, various publications, patents and published patent applications are cited. The disclosures of these publications, patents and published patent specification referenced in this application are hereby incorporated by reference into the present disclosure to more fully describe the state of the art to which this invention pertains.

SUMMARY OF THE INVENTION

APM1 belongs to an expanding family of related secreted polypeptides that includes among others C2P, ZADJ-2 and ZADJ-7. These polypeptides have in common the structure: signal peptide, N-terminally disposed unique region, collagen-like region, and globular C-terminal C1q homology domain. APM1, C2P, ZADJ-2 and ZADJ-7 further share an NGLXXD amino acid motif C-terminally disposed within the globular domain within a loop implicated in receptor binding, wherein said receptor is PROLIXIN. Fragments of APM1, C2P, ZADJ-2 and ZADJ-7 polypeptide comprising the globular domain are herein referred to as gAPM1, gC2P, gZADJ-2 and gZADJ-7. It is further taken to be understood herein that LIGAND refers to a composition consisting essentially of or consisting of in vitro or in vivo self-assembling homotrimer comprised of gAPM1, gC2P, gZADJ-2, or gZADJ-7 polypeptide fragment.

PROLAXIN is a member of the Tumor Necrosis Factor Receptor Super Family (TNFRSF) and is a Type m transmembrane protein. The instant invention is based on PROLIXIN as receptor for LIGAND that mediates effects, including utility for weight reduction, maintenance of weight loss, prevention of weight gain, increased insulin sensitivity, and control of blood glucose levels in humans and other mammals. These effects in mammals of PROLIXIN engagement by LIGAND also include reduction of elevated free fatty acid levels including elevated free fatty acid levels including elevated free fatty acid levels caused by administration of epinephrine, i.v. injection of "intralipid", or administration of a high fat test meal, as well as increased fatty acid oxidation in muscle cells, and weight reduction in mammals consuming a normal or high fat/high sucrose diet. More specifically, the present invention is directed to PROLIXIN to which LIGAND binds and through which LIGAND mediates said effects.

In particular, the invention provides for methods of identifying and using AGONISTS and ANTAGONISTS of PROLIXIN activity, wherein said activity is selected from the group consisting of lipid partitioning, lipid metabolism, and insulin-like activity, as well as to pharmaceutical and physiologically acceptable compositions comprising said PROLIXIN AGONISTS or ANTAGONISTS and methods of administering said pharmaceutical and physiologically acceptable compositions in order to increase or reduce body weight, maintain weight loss, or to treat obesity-related diseases and disorders. Assays for identifying AGONISTS and ANTAGONISTS of obesity-related activity are also part of the invention.

Preferably said PROLIXIN AGONIST or ANTAGONIST is a compound selected from the group consisting of polypeptide, polypeptide fragment, peptide, proein, antibody, carbohydrate, lipid, small molecular weight organic compound and small molecular weight inorganic compound.

Preferably said PROLIXIN AGONIST or ANTAGONIST is a compound that selectively binds to the extracellular domain of PROLIXIN.

In other embodiment, said PROLIXIN AGONIST or ANTAGONIST is a compound that selectively binds to the intracellular domain of a polypeptide comprising the extracellular domain of PROLIXIN.

The present invention also provides a method of assaying test compounds to identify a test compound that binds to PROLIXIN polypeptide. The method comprises contacting PROLIXIN polypeptide with a test compound and to determine the extent of binding of the test compound to said PROLIXIN polypeptide. The method further comprises determining whether such test compounds are AGONISTS or ANTAGONISTS of PROLIXIN polypeptide. The present invention further provides a method of testing the impact of molecules on the expression of PROLIXIN polypeptide or on the activity of PROLIXIN polypeptide.

The present invention also relates to diagnostic methods of identifying individuals or non-human animals having elevated or reduced levels of PROLIXIN products, which individuals are likely to benefit from therapies to suppress or enhance PROLIXIN expression, respectively, and to methods of identifying individuals or non-human animals at increased risk for developing, or present state of having, certain diseases/disorders associated with PROLIXIN abnormal expression or biological activity.

The present invention provides for methods of identifying AGONISTS of PROLIXIN polypeptide biological activity comprising contacting a small molecule compound with PROLIXIN polypeptides and measuring PROLIXIN polypeptide biological activity in the presence and absence of these small molecules. The present invention further provides for methods of identifying ANTAGONISTS of PROLIXIN polypeptide biological activity comprising contacting a small molecule compound with PROLIXIN polypeptides and measuring PROLIXIN polypeptide biological activity in the presence and absence of these small molecules. These small molecules can be a naturally occurring medicinal compound or derived from combinatorial chemical libraries.

The present invention also relates to pharmaceutical or physiologically acceptable compositions comprising, an active agent, including AGONIST or ANTAGONIST of the present invention.

In a first aspect, the invention is directed to PROLIXIN AGONISTS, wherein said AGONIST is an antibody that specifically binds PROLIXIN, a compound excluding said PROLIXIN antibody (e.g., small organic or inorganic compound, protein, peptide, carbohydrate, lipid), or a LIGAND polypeptide or fragment thereof.

In a further preferred embodiment, the invention is directed to a PROLIXIN AGONIST, wherein said AGONIST is an antibody that specifically binds PROLIXIN. More preferably the invention is directed to said PROLIXIN antibody, wherein said PROLIXIN antibody binds PROLIXIN and manifests LIGAND activity, wherein said activity is selected from the group consisting of lipid partitioning, lipid metabolism, and insulin-like activity or described herein.

In a further preferred embodiment, the invention is directed to a PROLIXIN AGONIST, wherein said AGONIST is a compound excluding said PROLIXIN antibody. More preferably the invention is directed to said compound, wherein said compound binds PROLIXIN and manifests LIGAND activity, wherein said activity is selected from the group consisting of lipid partitioning, lipid metabolism, and insulin-like activity or described herein. Further more preferably the invention is directed to said compound, wherein said compound manifests LIGAND activity exclusive of binding to PROLIXIN, wherein said activity is selected from the group consisting of lipid partitioning, lipid metabolism, and insulin-like activity or described herein. Further more preferably the invention is directed to said compound, wherein said compound increases PROLIXIN expression.

In a further preferred embodiment, the invention is directed to a PROLIXIN AGONIST that selectively binds to a polypeptide comprising the extracellular domain of PROLIXIN.

In a further preferred embodiment, the invention is directed to a PROLIXIN AGONIST, wherein said AGONIST is LIGAND, and wherein it is understood that LIGAND refers to a composition consisting essentially of or consisting of in vitro or in vivo self-assembling homotrimer comprised of gAPM1, gC2P, gZADJ-2, or gZADJ-7 polypeptide fragment. More preferably the invention is directed to said LIGAND, wherein said LIGAND binds PROLIXIN and elicits biological activity, wherein said activity is selected from the group consisting of lipid partitioning, lipid metabolism, and insulin-like activity or described herein. More preferably the invention is directed to said LIGAND, wherein said LIGAND induces, enhances, or potentiates said biological activity exclusive of binding to PROLIXIN. In preferred embodiment, said homotrimer is comprised of preferred gAPM1, gC2P, gZADJ-2 or gZADJ-7 polypeptide fragment.

APM1. Preferred gAPM1 polypeptide fragment is selected from amino acids 18-244, 34-244, 49-244, 56-244, 59-244, 66-244, 69-244, 78-244, 85-244, 93-244, 101-244, 102-244, 103-244, 104-244, 107-244, 110-244 or 113-244, wherein said numbering of said amino acids within APM1 amino acid sequence is understood to be taken from said APM1 amino acid sequence presented in Table 2. Less preferred gAPM1 fragments are indicated in bold.

C2P. Preferred gC2P polypeptide fragment is selected from amino acids 20-333, 25-333, 43-333, 45-333, 46-333, 50-333, 53-333, 61-333, 67-333, 74-333, 75-333, 77-333, 81-333, 82-333, 86-333, 89-333, 95-333, 100-333, 104-333, 113-333, 116-333, 125-333, 128-333, 140-333, 160-333, 164-333, 179-333, 182-333, 185-333, 188-333, 191-333, 193-333, or 202-333, wherein said numbering of said amino acids within C2P amino acid sequence is understood to be taken from said C2P amino acid sequence presented in Table 2. Less preferred gC2P fragments are indicated in bold.

ZADJ-2. Preferred gZADJ-2 polypeptide fragment is selected from amino acids 16-285, 25-285, 26-285, 29-285, 30-285, 91-285, 93-285, 97-285, 98-285, 99-285, 105-285, 109-285, 112-285, 120-285, 126-285, 127-285, 130-285, 132-285, 133-285, 134-285, or 150-285, wherein said numbering of said amino acids within ZADJ-2 amino acid sequence is understood to be taken from said ZADJ-2 amino acid sequence presented in Table 2. Less preferred gZADJ-2 fragments are indicated in bold.

ZADJ-7. Preferred gZADJ-7 polypeptide fragment is selected from amino acids 31-303, 39-303, 78-303, 81-303, 84-303, 85-303, 88-303, 91-303, 97-303, 99-303, 109-303, 117-303, 118-303, 127-303, 139-303, 142-303, 155-303, or 162-303, wherein said numbering of said amino acids within ZADJ-7 amino acid sequence is understood to be taken from said ZADJ-7 amino acid sequence presented in Table 2. Less preferred gZADJ-7 fragments are indicated in bold.

More Preferred LIGAND is APM1.

In a further preferred embodiment, said AGONIST is able to lower circulating (either blood, serum or plasma) levels (concentration) of: (i) free fatty acids, (ii) glucose, and/or (iii) triglycerides.

Further preferred AGONISTS are those that significantly stimulate muscle lipid or free fatty acid oxidation as compared to untreated cells. Further preferred AGONISTS are those that cause C2C12 cells differentiated in the presence of said AGONISTS to undergo at least 10%, 20%, 30%, 35%, or 40% more oleate oxidation as compared to untreated cells.

Further preferred AGONISTS are those that increase by at least 10%, 20%, 30%, 35%, or 40% leptin uptake in a liver cell line [preferably BPRCL mouse liver cells (ATCC CRL-2217)] as compared to untreated cells.

Further preferred AGONISTS are those that significantly reduce the postprandial increase in plasma free fatty acids or triglycerides, particularly following a high fat meal.

Further preferred AGONISTS are those that significantly reduce or eliminate ketone body production, particularly following a high fat meal.

Further preferred AGONISTS are those that increase glucose uptake in skeletal muscle cells.

Further preferred AGONISTS are those that increase glucose uptake in adipose cells.

Further preferred AGONISTS are those that increase glucose uptake in neuronal cells.

Further preferred AGONISTS are those that increase glucose uptake in red blood cells.

Further preferred AGONISTS are those that increase glucose uptake in the brain.

Further preferred AGONISTS are those that significantly reduce the postprandial increase in plasma glucose following a meal, particularly a high carbohydrate meal.

Further preferred AGONISTS are those that significantly prevent the postprandial increase in plasma glucose following a meal, particularly a high fat or a high carbohydrate meal.

Further preferred AGONISTS are those that improve insulin sensitivity.

Further preferred said AGONISTS are those that decrease body mass, wherein said decrease in body mass is comprised of a change in mass of the subcutaneous adipose tissue.

Further preferred said AGONISTS are those that decrease body mass, wherein said decrease in body mass is comprised of a change in mass of the visceral (omental) adipose tissue.

In a second aspect, the invention features a pharmaceutical or physiologically acceptable composition comprising, consisting essentially of, or consisting of, said AGONIST described in the first aspect and, alternatively, a pharmaceutical or physiologically acceptable diluent.

In a third aspect, the invention features a method of reducing body mass comprising providing or administering to individuals in need of reducing body mass said pharmaceutical or physiologically acceptable composition described in the second aspect.

In a fourth aspect, the invention features a method of preventing or treating an obesity-related disease or disorder comprising providing or administering to an individual in need of such treatment said pharmaceutical or physiologically acceptable composition described in the second aspect. Preferably, said obesity-related disease or disorder is selected from the group consisting of obesity, insulin resistance, atherosclerosis, atheromatous disease, heart disease, hypertension, stroke, Syndrome X, Noninsulin Dependent Diabetes Mellitus (NIDDM, or Type II diabetes) and Insulin Dependent Diabetes Mellitus (IDDM or Type I diabetes). Diabetes-related complications to be treated by the methods of the invention include microangiopathic lesions, ocular lesions, retinopathy, neuropathy, and renal lesions. Heart disease includes, but is not limited to, cardiac insufficiency, coronary insufficiency, and high blood pressure. Other obesity-related disorders to be treated by said PROLIXIN AGONIST of the invention include hyperlipidemia and hyperuricemia. In preferred embodiments, said individual is a mammal, preferably a human.

In related aspects, embodiments of the present invention includes methods of causing or inducing a desired biological response in an individual comprising the steps of: providing or administering to an individual a composition comprising AGONIST, wherein said biological response is selected from the group consisting of:
  (a) lowering circulating (either blood, serum, or plasma) levels (concentration) of free fatty acids;
  (b) lowering circulating (either blood, serum or plasma) levels (concentration) of glucose;
  (c) lowering circulating (either blood, serum or plasma) levels (concentration) of triglycerides;
  (d) stimulating muscle lipid or free fatty acid oxidation;
  (e) increasing leptin uptake in the liver or liver cells;
  (e) reducing the postprandial increase in plasma free fatty acids, particularly following a high fat meal;
  (f) reducing or eliminating ketone body production, particularly following a high fat meal;
  (g) increasing tissue sensitivity to insulin, particularly muscle, adipose, liver or brain, and further wherein said biological response is significantly greater than, or at least 10%, 20%, 30%, 35%, or 40% greater than that observed in the absence of treatment; or alternatively wherein said biological response is greater than a transient response; or alternatively wherein said biological response is sustained. In further preferred embodiments, the present invention of said pharmaceutical or physiologically acceptable composition can be used as a method to control blood glucose in some persons with Noninsulin Dependent Diabetes Mellitus (NIDDM, Type II diabetes) in combination with insulin therapy.

In further preferred embodiments, the present invention of said pharmaceutical or physiologically acceptable composition can be used as a method to control blood glucose in some persons with Insulin Dependent Diabetes Mellitus (IDDM, Type I diabetes) in combination with insulin therapy.

In further preferred embodiments, the present invention of said pharmaceutical or physiologically acceptable composition can be used as a method to control body weight in some persons with Noninsulin Dependent Diabetes Mellitus (NIDDM, Type II diabetes) in combination with insulin therapy.

In further preferred embodiments, the present invention of said pharmaceutical or physiologically acceptable composition can be used as a method to control body weight in some persons with Insulin Dependent Diabetes Mellitus (IDDM, Type I diabetes) in combination with insulin therapy.

In further preferred embodiments, the present invention of said pharmaceutical or physiologically acceptable composition can be used as a method to control blood glucose in some persons with Noninsulin Dependent Diabetes Mellitus (NIDDM, Type II diabetes) alone, without combination of insulin therapy.

In further preferred embodiments, the present invention of said pharmaceutical or physiologically acceptable composition can be used as a method to control blood glucose in some persons with Insulin Dependent Diabetes Mellitus (IDDM, Type I diabetes) alone, without combination of insulin therapy.

In further preferred embodiments, the present invention of said pharmaceutical or physiologically acceptable composition can be used as a method to control body weight in some persons with Noninsulin Dependent Diabetes Mellitus (NIDDM, Type II diabetes) alone, without combination of insulin therapy.

In further preferred embodiments, the present invention of said pharmaceutical or physiologically acceptable composition can be used as a method to control body weight in some persons with Insulin Dependent Diabetes Mellitus (IDDM, Type I diabetes) alone, without combination of insulin therapy.

In a further preferred embodiment, the present invention may be used in complementary therapy of NIDDM patients to improve their weight or glucose control in combination with an insulin secretagogue or an insulin sensitising agent. Preferably, the insulin secretagogue is 1,1-dimethyl-2-(2-morpholino phenyl)guanidine fumarate (BTS67582) or a sulphonylurea selected from tolbutamide, tolazamide, chlorpropamide, glibenclamide, glimepiride, glipizide and glidazide. Preferably, the insulin sensitising agent is selected from metformin, ciglitazone, troglitazone and pioglitazone.

The present invention further provides a method of improving the body weight or glucose control of NIDDM patients alone, without an insulin secretagogue or an insulin sensitising agent.

In a further preferred embodiment, the present invention may be used in complementary therapy of IDDM patients to improve their weight or glucose control in combination with an insulin secretagogue or an insulin sensitising agent. Preferably, the insulin secretagogue is 1,1-dimethyl-2-(2-morpholino phenyl) guanidine fumarate (BTS67582) or a sulphonylurea selected from tolbutamide, tolazamide, chlorpropamide, glibenclamide, glimepiride, glipizide and glidazide. Preferably, the insulin sensitising agent is selected from metformin, ciglitazone, troglitazone and pioglitazone.

The present invention further provides a method of improving the body weight or glucose control of IDDM patients alone, without an insulin secretagogue or an insulin sensitising agent.

In a further preferred embodiment, the present invention may be administered either concomitantly or concurrently, with the insulin secretagogue or insulin sensitising agent for example in the form of separate dosage units to be used simultaneously, separately or sequentially (either before or after the secretagogue or either before or after the sensitising agent). Accordingly, the present invention further provides for a composition of pharmaceutical or physiologically acceptable composition and an insulin secretagogue or insulin sensitising agent as a combined preparation for simultaneous, separate or sequential use for the improvement of body weight or glucose control in NIDDM or IDDM patients.

In further preferred embodiments, the present invention of said pharmaceutical or physiologically acceptable composition further provides a method for the use as an insulin sensitiser.

In further preferred embodiments, the present invention of said pharmaceutical or physiologically acceptable composition can be used as a method to improve insulin sensitivity in some persons with Noninsulin Dependent Diabetes Mellitus (NIDDM, Type II diabetes) in combination with insulin therapy.

In further preferred embodiments, the present invention of said pharmaceutical or physiologically acceptable composition can be used as a method to improve insulin sensitivity in some persons with Insulin Dependent Diabetes Mellitus (IDDM, Type I diabetes) in combination with insulin therapy.

In further preferred embodiments, the present invention of said pharmaceutical or physiologically acceptable composition can be used as a method to improve insulin sensitivity in some persons with Noninsulin Dependent Diabetes Mellitus (NIDDM, Type II diabetes) without insulin therapy.

In a fifth aspect, the invention features a use of AGONIST described in the first aspect for treatment of obesity-related diseases and disorders and/or reducing body mass. Preferably, said obesity-related diseases and disorders are selected from the group consisting of obesity, insulin resistance, atherosclerosis, atheromatous disease, heart disease, hypertension, stroke, Syndrome X, Noninsulin Dependent Diabetes Mellitus (NIDDM, or Type II diabetes) and Insulin Dependent Diabetes Mellitus (IDDM or Type I diabetes). Diabetes-related complications to be treated by the methods of the invention include microangiopathic lesions, ocular lesions, retinopathy, neuropathy, and renal lesions. Heart disease includes, but is not limited to, cardiac insufficiency, coronary insufficiency, and high blood pressure. Other obesity-related disorders to be treated by said AGONIST of the invention include hyperlipidemia and hyperuricemia.

In a sixth aspect, the invention features a use of AGONIST described in the first aspect for the preparation of a medicament for the treatment of obesity-related diseases and disorders and/or for reducing body mass. Preferably, said obesity-related disease or disorder is selected from the group consisting of obesity, insulin resistance, atherosclerosis, atheromatous disease, heart disease, hypertension, stroke, Syndrome X, Noninsulin Dependent Diabetes Mellitus (NIDDM, or Type II diabetes) and Insulin Dependent Diabetes Mellitus (IDDM or Type I diabetes). Diabetes-related complications to be treated by the methods of the invention include microangiopathic lesions, ocular lesions, retinopathy, neuropathy, and renal lesions. Heart disease includes, but is not limited to, cardiac insufficiency, coronary insufficiency, and high blood pressure. Other obesity-related disorders to be treated by compounds of the invention include hyperlipidemia and hyperuricemia. In preferred embodiments, said individual is a mammal, preferably a human.

In a seventh aspect, the invention provides AGONIST of the first aspect of the invention, or a composition of the second aspect of the invention, for use in a method of treatment of the human or animal body.

In an eighth aspect, the invention features methods of reducing body weight comprising providing to an individual said pharmaceutical or physiologically acceptable composition described in the second aspect, or AGONIST described in the first aspect. Where the reduction of body weight is practiced for cosmetic purposes, the individual has a BMI of at least 20 and no more than 25. In embodiments for the treatment of obesity, the individual may have a BMI of at least 20. One embodiment for the treatment of obesity provides for the treatment of individuals with BMI values of at least 25. Another embodiment for the treatment of obesity provides for the treatment of individuals with BMI values of at least 30. Yet another embodiment provides for the treatment of individuals with BMI values of at least 40.

In further embodiment, the invention features methods of maintaining weight loss comprising providing to an individual said pharmaceutical or physiologically acceptable composition.

In a ninth aspect, the invention features the pharmaceutical or physiologically acceptable composition described in the second aspect for reducing body mass and/or for treatment or prevention of obesity-related diseases or disorders. Preferably, said obesity-related disease or disorder is selected from the group consisting of obesity, insulin resistance, atherosclerosis, atheromatous disease, heart disease, hypertension, stroke, Syndrome X, Noninsulin Dependent Diabetes Mellitus (NIDDM, or Type II diabetes) and Insulin Dependent Diabetes Mellitus (IDDM or Type I diabetes). Diabetes-related complications to be treated by the methods of the invention include microangiopathic lesions, ocular lesions, retinopathy, neuropathy, and renal lesions. Heart disease includes, but is not limited to, cardiac insufficiency, coronary insufficiency, and high blood pressure. Other obesity-related disorders to be treated by compounds of the invention include hyperlipidemia and hyperuricemia. In preferred embodiments, said individual is a mammal, preferably a human. In preferred embodiments, the identification of said individuals to be treated with said pharmaceutical or physiologically acceptable composition comprises genotyping LIGAND single nucleotide polymorphisms (SNPs) or measuring LIGAND polypeptide or mRNA levels in clinical samples from said individuals. Preferably, said clinical samples are selected from the group consisting of blood, serum, plasma, urine, and saliva.

In a tenth aspect, the invention features the pharmaceutical or physiologically acceptable composition described in the second aspect for reducing body weight for cosmetic reasons.

In an eleventh aspect, AGONIST of the invention is used in methods of treating insulin resistance comprising providing to an individual said pharmaceutical or physiologically acceptable composition described in the second aspect, or AGONIST described in the first aspect.

In a preferred aspect of the methods above and disclosed herein, the amount of AGONIST administered to an individual is sufficient to bring levels of PROLIXIN activation to their normal levels (levels in individuals without obesity-related disease or disorder). "Normal levels" of PROLIXIN activation may be followed using surrogate markers including circulating (either blood, serum or plasma) levels (concentration) of: (i) free fatty acids, (ii) glucose, and/or (iii) triglycerides.

In a twelfth aspect, the invention is directed to a PROLIXIN ANTAGONIST, wherein said ANTAGONIST is a soluble fragment of PROLIXIN polypeptide, an antibody that specifically binds PROLIXIN, a compound excluding said soluble fragment of PROLIXIN polypeptide and said PROLIXIN antibody (e.g., small molecular weight organic or inorganic compound, protein, peptide, carbohydrate, lipid), or a variant or fragment of LIGAND polypeptide.

In a further preferred embodiment, the invention is directed to a PROLIXIN ANTAGONIST, wherein said ANTAGONIST is a soluble fragment of PROLIXIN polypeptide. More preferably the invention is directed to purified, isolated, or recombinant soluble fragments of PROLIXIN polypeptide. More preferably the invention is directed to said soluble fragment of PROLIXIN polypeptide, wherein said soluble fragment binds LIGAND and blocks LIGAND activity, said activity being selected from the group consisting of lipid partitioning, lipid metabolism, and insulin-like activity or described herein, and wherein said soluble fragment of PROLIXIN polypeptide does not activate PROLIXIN. Preferably said soluble fragment of PROLIXIN polypeptide blocks or inhibits LIGAND binding to PROLIXIN. In preferred embodiments, said soluble fragment of PROLIXIN polypeptide comprises, consists essentially of, or consists of, at least 6 and not more than 76 consecutive amino acids of SEQ ID NO:2, more preferably of amino acids comprising the extracellular domain of PROLIXIN. Preferred said soluble fragment of PROLIXIN comprises the extracellular domain of mature PROLIXIN polypeptide. Particularly preferred soluble fragment of PROLIXIN comprises amino acids 1-39, 2-39, 1-42, 2-42, 1-44, 2-44, 1-51, 2-51, 1-54, 2-54, 1-58, 2-58, 1-63, 2-63, 1-67, 2-67, 1-72, 2-72, 1-76 or 2-76 of SEQ ID NO:2. In other preferred embodiments, said soluble fragment of PROLIXIN polypeptide comprises an amino acid sequence at least 80%, 85%, 90%, 91%, 92%, 93%, 94%, 95%, 96%, 97%, 98%, or 99% identical to the corresponding consecutive amino acids of SEQ ID NO:2. Further preferred embodiments include heterologous polypeptides comprising a PROLIXIN polypeptide of the invention. In further preferred embodiment, a PROLIXIN polypeptide of the invention is conjugated at its N- or C-terminus to an antibody Fc region or portion thereof.

In a further preferred embodiment, the invention is directed to a PROLIXIN ANTAGONIST, wherein said ANTAGONIST is an antibody that specifically binds PROLIXIN. More preferably the invention is directed to said PROLIXIN antibody, wherein said PROLIXIN antibody binds PROLIXIN and blocks LIGAND activity, said activity being selected from the group consisting of lipid partitioning, lipid metabolism, and insulin-like activity or described herein, and wherein said PROLIXIN antibody does not activate PROLIXIN. Preferably said PROLIXIN antibody blocks or inhibits LIGAND binding to PROLIXIN.

In a further preferred embodiment, the invention is directed to a PROLIXIN ANTAGONIST, wherein said ANTAGONIST is a compound excluding said soluble fragment of PROLIXIN polypeptide and said PROLIXIN antibody (e.g., small organic molecule, protein, peptide). More preferably the invention is directed to said compound, wherein said compound binds to PROLIXIN and blocks LIGAND activity, said activity being selected from the group consisting of lipid partitioning, lipid metabolism, and insulin-like activity or described herein, and wherein said compound does not activate PROLIXIN. Preferably said compound that binds to PROLIXIN blocks or inhibits LIGAND binding to PROLIXIN. Further more preferably the invention is directed to said compound, wherein said compound blocks or inhibits LIGAND activity exclusive of binding to PROLIXIN, said activity being selected from the group consisting of lipid partitioning, lipid metabolism, and insulin-like activity or described herein, and wherein said compound does not activate PROLIXIN. Further more preferably the invention is directed to said compound, wherein said compound blocks or inhibits PROLIXIN expression and wherein said compound does not have LIGAND activity, said activity being selected from the group consisting of lipid partitioning, lipid metabolism, and insulin-like activity or described herein, and wherein said compound does not activate PROLIXIN.

In a further preferred embodiment, the invention is directed to a PROLIXIN ANTAGONIST, wherein said ANTAGONIST is a variant or fragment of LIGAND polypeptide. More preferably the invention is directed to said variant of fragment of LIGAND polypeptide, wherein said variant or fragment of LIGAND polypeptide binds PROLIXIN and blocks LIGAND activity, said activity being selected from the group consisting of lipid partitioning, lipid metabolism, and insulin-like activity or described herein, and wherein said variant or fragment of LIGAND polypeptide does not activate PROLIXIN. Preferably said variant or fragment of LIGAND polypeptide blocks or inhibits LIGAND binding to PROLIXIN. More preferably the invention is directed to said variant or fragment of LIGAND polypeptide, wherein said variant or fragment of LIGAND polypeptide inhibits the induction, enhancement, or potentiation of said biological activity exclusive of binding to PROLIXIN.

In a further preferred embodiment, the invention is directed to a PROLIXIN ANTAGONIST that selectively binds to a polypeptide comprising the extracellular domain of PROLIXIN.

In a further preferred embodiment, said ANTAGONIST is able to raise circulating (either blood, serum or plasma) levels (concentration) of: (i) free fatty acids, (ii) glucose, and/or (iii) triglycerides.

Further preferred said ANTAGONISTS are those that significantly inhibit muscle lipid or free fatty acid oxidation stimulated by its LIGAND. Further preferred said ANTAGONISTS are those that cause C2C12 cells differentiated in the presence of LIGAND to undergo at least 10%, 20%, 30%, 35%, or 40% less oleate oxidation as compared to untreated cells.

Further preferred said ANTAGONISTS are those that inhibit by at least 10%, 20%, 30%, 35%, or 40% the increase in leptin uptake stimulated by LIGAND polypeptide in a liver cell line [preferably BPRCL mouse liver cells (ATCC CRL-2217)] as compared to untreated cells.

Further preferred said ANTAGONISTS are those that significantly increase the postprandial increase in plasma free fatty acids, particularly following a high fat meal.

Further preferred said ANTAGONISTS are those that significantly increase ketone body production, particularly following a high fat meal.

Further preferred said ANTAGONISTS are those that decrease glucose uptake in skeletal muscle cells stimulated by LIGAND.

Further preferred said ANTAGONISTS are those that decrease glucose uptake in adipose cells stimulated by LIGAND.

Further preferred said ANTAGONISTS are those that decrease glucose uptake in neuronal cells stimulated by LIGAND.

Further preferred said ANTAGONISTS are those that decrease glucose uptake in red blood cells stimulated by LIGAND.

Further preferred said ANTAGONISTS are those that decrease glucose uptake in the brain stimulated by LIGAND.

Further preferred said ANTAGONISTS are those that significantly increase the postprandial increase in plasma glucose following a meal, particularly a high carbohydrate meal.

Further preferred said ANTAGONISTS are those that significantly facilitate the postprandial increase in plasma glucose following a meal, particularly a high fat or a high carbohydrate meal.

Further preferred said ANTAGONISTS are those that reduce the insulin sensitivity stimulated by LIGAND.

Further preferred said ANTAGONISTS are those that increase body mass, wherein said increase in body mass is comprised of a change in mass of the subcutaneous adipose tissue.

Further preferred said ANTAGONISTS are those that increase body mass, wherein said increase in body mass is comprised of a change in mass of the visceral (omental) adipose tissue.

In a thirteenth aspect, the invention features a pharmaceutical or physiologically acceptable composition comprising, consisting essentially of, or consisting of, said ANTAGONIST described in the twelfth aspect and, alternatively, a pharmaceutical or physiologically acceptable diluent.

In a fourteenth aspect, the invention features a method of increasing body mass comprising providing or administering to individuals in need of increasing body mass said pharmaceutical or physiologically acceptable composition described in the thirteenth aspect.

In a fifteenth aspect, the invention features a method of preventing or treating disorders associated with excessive weight loss comprising providing or administering to an individual in need of such treatment said pharmaceutical or physiologically acceptable composition described in the thirteenth aspect. Preferably said disorder is selected from the group consisting of cachexia, wasting, cancer-related weight loss, AIDS-related weight loss, chronic inflammatory disease-related weight loss, anorexia, and bulimia. Said disorders associated with excessive weight loss are comprised of those mediated by tumor necrosis factor (TNFalpha) alone, those mediated by TNFalpha plus one or more additional factors, and those mediated only by one or more factors exclusive of TNFalpha. Said factors include, but are not restricted to, macrophage migration inhibitory factor, interleukin 1, and interleukin 6. In preferred embodiments, said individual is a mammal, preferably a human.

In related aspects, embodiments of the present invention includes methods of causing or inducing a desired biological response in an individual comprising the steps of: providing or administering to an individual a composition comprising ANTAGONIST, wherein said biological response is selected from the group consisting of:

(a) raising circulating (either blood, serum, or plasma) levels (concentration) of free fatty acids (FFA) or triglycerides (TG);
(b) raising circulating (either blood, serum or plasma) levels (concentration) of glucose;
(c) raising circulating (either blood, serum or plasma) levels (concentration) of triglycerides;
(d) inhibiting muscle lipid or free fatty acid oxidation;
(c) inhibiting leptin uptake in the liver or liver cells;
(e) increasing the postprandial increase in plasma free fatty acids, particularly following a high fat meal; and,
(f) increasing or eliminating ketone body production, particularly following a high fat meal;
(g) reducing tissue sensitivity to insulin, particularly muscle, adipose, liver or brain, and further wherein said biological response is greater than a transient response; or alternatively wherein said biological response is sustained. In further preferred embodiments, the present invention of said pharmaceutical or physiologically acceptable composition can be used as a method of increasing body mass in some persons with cachexia, wasting, cancer-related weight loss, AIDS-related weight loss, chronic inflammatory disease-related weight loss, anorexia, and bulimia.

In further preferred embodiments, the present invention of said pharmaceutical or physiologically acceptable composition further provides a method for the use as an insulin de-sensitiser, wherein the sensitivity of a cell or tissue to insulin is reduced.

In a sixteenth aspect, the invention features a method of making the PROLIXIN polypeptide described in the twelfth aspect, wherein said method is selected from the group consisting of proteolytic cleavage, recombinant methodology and artificial synthesis. In a preferred embodiment, proteolytic cleavage is carried out using trypsin, plasmin, or collagenase.

In a seventeenth aspect, the invention features a use of ANTAGONIST described in the twelfth aspect for the preparation of a medicament for the treatment of disorders associated with excessive weight loss and/or for increasing body mass. Preferably, said disorder is selected from the group consisting of cachexia, wasting, cancer-related weight loss, AIDS-related weight loss, chronic inflammatory disease-related weight loss, anorexia, and bulimia. In preferred embodiments, said individual is a mammal, preferably a human.

In an eighteenth aspect, the invention provides ANTAGONIST of the twelfth aspect of the invention, or a composition of the thirteenth aspect of the invention, for use in a method of treatment of the human or animal body.

In a nineteenth aspect, the invention features methods of increasing body weight comprising providing to an individual said pharmaceutical or physiologically acceptable composition described in the thirteenth aspect, or ANTAGONIST described in the twelfth aspect. Where the increase of body weight is practiced for cosmetic purposes, the individual has a BMI of no greater than 25 and at least 20. In embodiments for the treatment of disorders associated with excessive weight loss, the individual may have a BMI no greater than 20. One embodiment for the treatment of disorders associated with excessive weight loss provides for the treatment of individuals with BMI values of no greater than 15. Alternatively, for increasing the body weight of an individual, the BMI value should be at least 15 and no more than 20.

In a twentieth aspect, the invention features the pharmaceutical or physiologically acceptable composition described in the thirteenth aspect for increasing body mass and/or for treatment of disorders associated with excessive weight loss. Preferably, said disorder is selected from the group consisting of cachexia, wasting, cancer-related weight loss, AIDS-related weight loss, chronic inflammatory disease-related weight loss, anorexia, and bulimia. In preferred embodiments, said individual is a mammal, preferably a human.

In a twenty-first aspect, the invention features the pharmaceutical or physiologically acceptable composition described in the thirteenth aspect for increasing body weight for cosmetic reasons.

In a preferred aspect of the methods above and disclosed herein, the amount of ANTAGONIST administered to an individual is sufficient to bring levels of PROLIXIN activation to their normal levels (levels in healthy individuals). "Normal levels" of PROLIXIN activation may be followed using surrogate markers including circulating (either blood, serum or plasma) levels (concentration) of: (i) free fatty acids, (ii) glucose, and/or (iii) triglycerides.

Brief Description of Tables

Table 1 lists known or predicted biologic structural and functional domains for the PROLIXIN polypeptide of SEQ ID NO:2 of the present invention, including the extracellular (EC) domain, transmembrane domain, and intracellular (IC) domain.

Table 2 lists the amino acid sequence of full-length APM1 (SEQ ID NO: 3), C2P (SEQ ID NO: 4), ZADJ-2 (SEQ ID NO: 5) and ZADJ-7 (SEQ ID NO: 6) polypeptide. The total number of amino acids is given in parentheses. The predicted signal peptide is indicated in bold. The collagen-like region is indicated by dotted line. The region between the predicted signal peptide and the collagen-like region is the N-terminally disposed unique region. The globular C-terminal C1q homology domain is indicated by single underline. The NGLXXD amino acid motif C-terminally disposed within the globular domain is indicated by double underline. It is taken to be understood that C2P herein encompasses variants comprising the substitution of valine for methionine at position 219 and/or the substitution of methionine for valine at position 301.

Structure of PROLIXIN Polypeptide

The full-length PROLIXIN polypeptide is comprised of at least 3 distinct regions including:
1. an extracellular domain comprising a LIGAND binding portion and comprising amino acids from about amino acids 1-76 of SEQ ID NO:2;
2. a transmembrane domain comprising amino acids from about amino acids 77-99 of SEQ ID NO:2; and
3. an intracellular domain comprising amino acids from about amino acids 100-184 of SEQ ID NO:2.

Brief Description of Sequence Listing

SEQ ID NO: 1 is the nucleotide sequence of cDNA with an open reading frame which location is indicated as features. When appropriate, the locations of the potential polyadenylation site and polyadenylation signal are also indicated.

SEQ ID NO:2 is the amino acid sequence of polypeptide encoded by the cDNA of SEQ ID NO:1.

SEQ ID NO: 3 is the amino acid sequence of the full-length APM1 polypeptide.

SEQ ID NO: 4 is the amino acid sequence of the full-length C2P polypeptide.

SEQ ID NO: 5 is the amino acid sequence of the full-length ZADJ-2 polypeptide.

SEQ ID NO: 6 is the amino acid sequence of the full-length ZADJ-7 polypeptide.

The appended Sequence Listing is hereby incorporated by reference in its entirety.

DETAILED DESCRIPTION

Definitions

Before describing the invention in greater detail, the following definitions are set forth to illustrate and define the meaning and scope of the terms used to describe the invention herein.

The term "isolated" requires that the material be removed from its original environment (e.g., the natural environment if the material is naturally occurring).

The term "purified" does not require absolute purity; rather, it is intended as a relative definition. Purification of starting material or natural material to at least one order of magnitude, preferably two or three orders, and more preferably four or five orders of magnitude is expressly contemplated.

As used interchangeably herein, the term "polynucleotide(s)" include RNA or DNA (either single or double stranded, coding, complementary or antisense), or RNA/DNA hybrid sequences of more than one nucleotide in either single chain or duplex form (although each of the above species may be particularly specified).

The terms "complementary" or "complement thereof" are used herein to refer to the sequences of polynucleotides that are capable of forming Watson & Crick base pairing with another specified polynucleotide throughout the entirety of the complementary region.

The terms "polypeptide" and "protein", used interchangeably herein, refer to a polymer of amino acids without regard to the length of the polymer; thus, peptides, oligopeptides, and proteins are included within the definition of polypeptide. This term also does not specify or exclude chemical or post-expression modifications of the polypeptides of the invention, although chemical or post-expression modifications of these polypeptides may be included excluded as specific embodiments.

As used herein, the terms "recombinant polynucleotide" and "polynucleotide construct" are used interchangeably to refer to linear or circular, purified or isolated polynucleotides that have been artificially designed and which comprise at least two nucleotide sequences that are not found as contiguous nucleotide sequences in their initial natural environment. In particular, these terms mean that the polynucleotide or cDNA is adjacent to "backbone" nucleic acid to which it is not adjacent in its natural environment.

The term "recombinant polypeptide" is used herein to refer to polypeptides that have been artificially designed and which comprise at least two polypeptide sequences that are not found as contiguous polypeptide sequences in their initial natural environment, or to refer to polypeptides which have been expressed from a recombinant polynucleotide.

As used herein, the term "operably linked" refers to a linkage of polynucleotide elements in a functional relationship.

As used herein, the term "non-human animal" refers to any non-human animal, including insects, birds, rodents and more usually mammals. Both the terms "animal" and "mammal" expressly embrace human subjects unless preceded with the term "non-human".

The term "domain" refers to an amino acid fragment with specific biological properties. This term encompasses all known structural and linear biological motifs.

As used herein, the term "receptor" refers to a polypeptide to which a "ligand" binds and through which said "ligand" elicits a biological response comprised of biological activities. Said receptor is preferably PROLIXIN of the present invention. Said "ligand" is preferably LIGAND of the present invention. By "receptor activation" is intended "ligand"-mediated alteration of said receptor polypeptide, wherein said alteration is selected from but not limited to the group consisting of receptor alterations associated with said biological response.

As used herein, the term "AGONIST" refers to naturally occurring and synthetic compounds capable of inducing, enhancing, or potentiating a biological response comprised of biological activities.

As used herein, the term "ANTAGONIST" refers to naturally occurring and synthetic compounds capable of inhibiting a biological response, inhibiting the induction of a biological response, or inhibiting the potentiation of a biological response, wherein said biological response is comprised of biological activities.

Without being limited by theory, the compounds/polypeptides of the invention are capable of modulating the partitioning of dietary lipids between the liver and peripheral tissues, and are thus believed to treat "diseases involving the partitioning of dietary lipids between the liver and peripheral tissues." The term "peripheral tissues" is meant to include muscle and adipose tissue. In preferred embodiments, the compounds/polypeptides of the invention partition the dietary lipids toward or away from the muscle. In alternative preferred embodiments, the dietary lipids are partitioned toward or away from the adipose tissue. In other preferred embodiments, the dietary lipids are partitioned toward or away from the liver. In yet other preferred embodiments, the compounds/polypeptides of the invention increase or decrease the oxidation of dietary lipids, preferably free fatty acids (FFA) by the muscle. Dietary lipids include, but are not limited to triglycerides and free fatty acids.

Preferred diseases believed to involve the partitioning of dietary lipids include obesity-related diseases and disorders such as obesity, insulin resistance, atherosclerosis, atheromatous disease, heart disease, hypertension, stroke, Syndrome X, Noninsulin Dependent Diabetes Mellitus (NIDDM, or Type II diabetes) and Insulin Dependent Diabetes Mellitus (IDDM or Type I diabetes). Diabetes-related complications to be treated by the methods of the invention include microangiopathic lesions, ocular lesions, retinopathy, neuropathy, and renal lesions. Heart disease includes, but is not limited to, cardiac insufficiency, coronary insufficiency, and high blood pressure. Other obesity-related disorders to be treated by compounds of the invention include hyperlipidemia and hyperuricemia. Yet other disorders of the invention include disorders associated with excessive weight loss such as cachexia, wasting, cancer-related weight loss, AIDS-related weight loss, chronic inflammatory disease-related weight loss, anorexia, and bulimia.

The terms "comprising", "consisting of" and "consisting essentially of" may be interchanged for one another throughout the instant application, although each retains its normal definition. The term "having" has the same meaning as "comprising" and may be replaced with either the term "consisting of" or "consisting essentially of".

Polypeptides of the Invention

Preferably, polypeptides of the invention are recombinantly produced using routine expression methods known in the art. The polynucleotide encoding the desired polypeptide is operably linked to a promoter into an expression vector suitable for any convenient host. Both eukaryotic and prokaryotic host systems are used in forming recombinant polypeptides. The polypeptide is then isolated from lysed cells or from the culture medium and purified to the extent needed for its intended use.

Consequently, a further embodiment of the present invention is a method of making a polypeptide, said method comprising the steps of
   a) obtaining a cDNA encoding said polypeptide;
   b) inserting said cDNA in an expression vector such that the cDNA is operably linked to a promoter; and
   c) introducing said expression vector into a host cell whereby said host cell produces said polypeptide.

In one aspect of this embodiment, the method further comprises the step of isolating the polypeptide. Another embodiment of the present invention is a polypeptide obtainable by the method described in the preceding paragraph.

The expression vector is any of the mammalian, yeast, insect or bacterial expression systems known in the art. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). In preferred embodiment, recombinant polypeptides of the invention are expressed in mammalian cells.

The invention is drawn, inter alia, to isolated, purified or recombinant polypeptides. PROLIXIN polypeptides of the invention are useful for increasing (ANTAGONISTS of PROLIXIN body weight either as a cosmetic treatment or for treatment or prevention of diseases and disorders as discussed or described herein. PROLIXIN polypeptides are also useful inter alia in screening assays for AGONISTS or ANTAGONISTS of PROLIXIN activity and for raising PROLIXIN-specific antibodies. When used for cosmetic treatments, or for the treatment or prevention of diseases, disorders, or conditions, one or more PROLIXIN polypeptides can be provided to a subject. Thus, various fragments of the full-length protein can be combined into a "cocktail" for use in the various treatment regimens. LIGAND polypeptides of the invention are useful for reducing (AGONISTS of PROLIXIN) body weight either as a cosmetic treatment or prevention of diseases and disorders as discussed or described herein.

The PROLIXIN polypeptides of the present invention are preferably provided in an isolated form, and may be partially or substantially purified.

Modifying PROLIXIN Biological Activity

Modifying endogenous PROLIXIN biological activity is expressly contemplated by the present invention. The present invention further relates to compounds able to modulate PROLIXIN biological activity and methods to use these compounds. Such compounds may interact with PROLIXIN polypeptides directly or indirectly.

Candidate AGONISTS and ANTAGONISTS Obtained by Optical Biosensor Methods

Compounds interacting with a polypeptide comprising PROLIXIN extracellular domain can be screened by using an Optical Biosensor as described in Edwards and Leatherbarrow (1997) and also in Szabo et al. (1995), the disclosures of which are incorporated by reference. This technique permits the detection of interactions between molecules in real time, without the need of labeled molecules. This technique, which is based on the surface plasmon resonance (SPR) phenomenon, is presented in more detail in Example 1.

Compounds Modulating PROLIXIN Biological Activity

Another method of screening for compounds that modulate PROLIXIN biological activity is by measuring the effects of test compounds on specific biological activity, wherein said activity is selected from the group consisting of lipid partitioning, lipid metabolism, and insulin-like activity or as described herein, in a host cell. In one embodiment, the present invention relates to a method of identifying an agent that alters PROLIXIN activity, wherein a nucleic acid construct comprising the polynucleotide of SEQ ID NO: 1 or a fragment thereof encoding full-length PROLIXIN polypeptide is introduced into a mammalian host cell. The transfected mammalian host cells are maintained under conditions appropriate for expression of the encoded PROLIXIN, whereby the nucleic acid is expressed. The host cells are then contacted with a compound to be assessed (an agent) and an activity of the cells is detected in the presence of the compound to be assessed, wherein said activity is selected from the group consisting of lipid partitioning, lipid metabolism, and insulin-like activity or as described herein. Detection of a change in said activity for said transfected host cell, but not in untransfected host cell, in the presence of the agent indicates that the agent alters PROLIXIN activity. In a particular embodiment, the invention relates to a method of identifying an agent which is an activator (AGONIST) of PROLIXIN activity, wherein detection of an increase of said activity, said activity being selected from the group consisting of lipid partitioning, lipid metabolism, and insulin-like activity or as described herein, in the presence of the agent indicates that the agent activates PROLIXIN activity. In another particular embodiment, the invention relates to a method of identifying an agent which is an inhibitor (ANTAGONIST) of PROLIXIN activity, wherein detection of a decrease of said activity, said activity being selected from the group consisting of lipid partitioning, lipid metabolism, and insulin-like activity or as described herein, in the presence of the agent indicates that the agent inhibits PROLIXIN activity.

Detection of a change in said PROLIXIN activity, said activity being selected from the group consisting of lipid partitioning, lipid metabolism, and insulin-like activity or as described herein, can be performed using a variety of techniques as described for representative activities in Examples provided herein.

In a particular embodiment a high throughput screen can be used to identify agents that activate (enhance) or inhibit PROLIXIN activity (See e.g., PCT publication WO 98/45438, which disclosure is hereby incorporated by reference in its entirety).

Methods of Screening for Compounds Modulating PROLIXIN Activity

The preset invention also relates to methods of screening compounds for their ability to modulate (e.g. increase or inhibit) the activity or expression of PROLIXIN. More specifically, the present invention relates to methods of testing compounds for their ability either to increase or to decrease activity of PROLIXIN. The assays are performed in vitro or in vivo.

The present invention relates to a method for the screening of a candidate substance for interaction with a polypeptide comprising PROLIXIN extracellular domain, said method comprising the following steps:
a) providing said polypeptide comprising PROLIXIN extracellular domain;
b) obtaining a candidate substance;
c) bringing into contact said polypeptide with said candidate substance;
d) detecting the complexes formed between said polypeptide and said candidate substance.

The invention further relates to a method for the production of a pharmaceutical composition comprising a method for the screening of a candidate substance that interact with a PROLIXIN polypeptide, fragments or variants thereof and furthermore mixing the identified substance with a pharmaceutically acceptable carrier.

The present invention relates to a method for the screening of a candidate substance for the capacity to increase expression of PROLIXIN, said method comprising the following steps:
a) isolating mRNA from cells which have or have not been contacted with said candidate substance;
b) carrying out a Northern blot analysis with labeled cDNA probe encoding all or part of PROLIXIN polypeptide;
c) wherein increased signal in cells having been contacted with said candidate substance over that of uncontacted cells is taken to indicate that said candidate substance increases expression of PROLIXIN and is an AGONIST of PROLIXIN activity; and d) wherein decreased signal in cells having been contacted with said candidate substance over that of uncontacted cells is taken to indicate that said candidate substance decreases expression of PROLIXIN and is an ANTAGONIST of PROLIXIN activity.

Methods of isolating mRNA and carrying out Northern blot analysis are well known to those of ordinary skill in the art.

Preparation of Antibody Compositions

Substantially pure protein or polypeptide is isolated from transfected or transformed cells containing an expression vector encoding the PROLIXIN protein or a portion thereof. The concentration of protein in the final preparation is adjusted, for example, by concentration on an Amicon filter device, to the level of a few micrograms/ml. Monoclonal or polyclonal antibody to the protein can then be prepared by methods well known to those of ordinary skill in the art.

Preferably the present invention includes monoclonal and polyclonal antibodies that specifically bind PROLIXIN polypeptide fragment comprising the extracellular domain of mature PROLIXIN polypeptide. Particularly preferred soluble fragment of PROLIXIN comprises amino acids 1-39, 2-39, 1-42, 2-42, 1-44, 2-44, 1-51, 2-51, 1-54, 2-54, 1-58, 2-58, 1-63, 2-63, 1-67, 2-67, 1-72, 2-72, 1-76 or 2-76 of SEQ ID NO:2.

EXAMPLES

The following Examples are provided for illustrative purposes and not as a means of limitation. One of ordinary skill in the art would be able to design equivalent assays and methods based on the disclosure herein all of which form part of the instant invention.

Example 1

Use of Biacore Technology to Detect Specific Binding of a Test Compound to Polypeptide Fragment Comprising PROLIXIN Extracellular Domain Biacore utilizes a biosensor technology for monitoring interactions between two or more molecules in real time, without the use of labels. The molecular classes than can be studied are diverse, ranging from proteins, peptides, nucleic acids, carbohydrates, and lipids to low molecular weight substances and pharmaceuticals.

The detection principle is based on the optical phenomena of surface plasmon resonance, which detects changes in refractive index close to a biosensor surface. In a typical experiment one of the interacting molecules is immobilized or captured (here, polypeptide fragment comprising PROLIXIN extracellular domain) to a flexible dextran layer close to the sensor surface. The interacting partner (here, test compound) is flowed across that surface. If an interaction occurs between the two molecules, there is a resulting increase in signal due to the increase in mass at the chip surface.

Soluble polypeptide fragment comprising PROLIXIN extracellular domain is attached to the sensor surface via amine coupling chemistry. The dextran is activated using N-hydroxysuccinimide and N-ethyl-N'-(3-dimethylaminopropyl)-carbodiimide hydrochloride for 7 minutes. Said PROLIXIN polypeptide fragment is diluted in 10 mM Na Acetate pH 5.0 at a concentration of 10 μg/ml and injected over the activated surface for 7 minutes. The surface is then blocked for 7 minutes using ethanolamine to remove any remaining esters. A blank flow cell absent said PROLIXIN polypeptide fragment is set up in parallel and used as a control surface. The running buffer is HBS-EP (0.01M HEPES pH 7.4, 0.15M NaCl, 3 mM EDTA, 0.005% Surfactant P20) and the instrument temperature is 25° C.

The test compound is filtered through an Ultrafree-0.5 Centrifugal Filter Device and resuspended in HBS-EP running buffer. The test compound is then diluted 1:10 in HBS-EP and injected over the said PROLIXIN polypeptide fragment surface and the blank control surface for 1 minute at a flow rate of 50 μl/min. The sensorgrams from the receptor surface and the control surface are aligned and overlayed.

To obtain the specific binding, the control surface was subtracted from the active surface comprised of said PROLIXIN polypeptide fragment.

Example 2

Effect of LIGAND on Muscle Cell Fatty Acid Oxidation

C2C12 cells are differentiated in the presence or absence of 2 μg/mL LIGAND for 4 days. On day 4, oleate oxidation rates are determined by measuring conversion of 1-$^{14}$C-oleate (0.2 mM) to $^{14}CO_2$ for 90 min. This experiment can be used to screen for active polypeptides and peptides as well as AGONISTS and ANTAGONISTS or activators and inhibitors of LIGAND receptor.

The effect of LIGAND on the rate of oleate oxidation can be compared in differentiated C2C12 cells (murine skeletal muscle cells; ATCC, Manassas, Va. CRL-1772) and in a hepatocyte cell line (Hepal-6; ATCC, Manassas, Va. CRL-1830). Cultured cells are maintained according to manufacturer's instructions. The oleate oxidation assay is performed as previously described (Muoio et al (1999) Biochem J 338;783-791). Briefly, nearly confluent myocytes are kept in low serum differentiation media (DMEM, 2.5% Horse serum) for 4 days, at which time formation of myotubes became maximal. Hepatocytes are kept in the same DMEM medium supplemented with 10% FCS for 2 days. One hour prior to the experiment the media is removed and 1 mL of preincubation media (MEM, 2.5% Horse serum, 3 mM glucose, 4 mM Glutamine, 25 mM Hepes, 1% FFA free BSA, 0.25 mM Oleate, 5 μg/mL gentamycin) is added. At the start of the oxidation experiment $^{14}$C-Oleic acid (1 μCi/mL, American Radiolabelled Chemical Inc., St. Louis, Mo.) is added and cells are incubated for 90 min at 37° C. in the absence/presence of 2.5 μg/mL LIGAND. After the incubation period 0.75 mL of the media is removed and assayed for $^{14}$C-oxidation products as described below for the muscle FFA oxidation experiment.

Example 3

Effect of LIGAND on In Vitro Glucose Uptake by Muscle Cells

L6 Muscle cells are obtained from the European Culture Collection (Porton Down) and are used at passages 7-11. Cells are maintained in standard tissue culture medium DMEM, and glucose uptake is assessed using [$^3$H]-2-deoxy-glucose (2DG) with or without LIGAND in the presence or absence of insulin ($10^{-8}$ M) as has been previously described (Walker, P. S. et al. (1990) Glucose transport activity in L6 muscle cells is regulated by the coordinate control of sub-cellular glucose transporter distribution, biosynthesis, and mRNA transcription. JBC 265(3):1516-1523; and Kilp, A. et al. (1992) Stimulation of hexose transport by metformin in L6 muscle cells in culture. Endocrinology 130(5):2535-2544, which discloses are hereby incorporated by reference in their entireties). Uptake of 2DG is expressed as the percentage change compared with control (no added insulin or LIGAND). Values are presented as mean±SEM of sets of 4 wells per experiment. Differences between sets of wells are evaluated by Student's t test, probability values $p<0.05$ are considered to be significant.

Example 4

Effect of LIGAND on Mice Fed a High-Fat Diet

Experiments are performed using approximately 6 week old C57B1/6 mice (8 per group). All mice are housed individually. The mice are maintained on a high fat diet throughout each experiment. The high fat diet (cafeteria diet; D12331 from Research Diets, Inc.) has the following composition: protein kcal % 16, sucrose kcal % 26, and fat kcal % 58. The fat is primarily composed of coconut oil, hydrogenated.

After the mice are fed a high fat diet for 6 days, micro-osmotic pumps are inserted using isoflurane-anesthesia, and are used to provide LIGAND, saline, and an irrelevant peptide to the mice subcutaneously (s.c.) for 18 days. LIGAND is provided at doses of 100, 50, 25, and 2.5 µg/day and the irrelevant peptide is provided at 10 µg/day. Body weight is measured on the first, third and fifth day of the high fat diet, and then daily after the start of treatment. Final blood samples are taken by cardiac puncture and are used to determine triglyceride (TG), total cholesterol (TC), glucose, leptin, and insulin levels. The amount of food consumed per day is also determined for each group.

Example 5

Effect of LIGAND on Plasma Free Fatty Acid in C57 BL/6 Mice

The effect of LIGAND on postprandial lipemia (PPL) in normal C57BL6/J mice is tested.

The mice used in this experiment are fasted for 2 hours prior to the experiment after which a baseline blood sample is taken. All blood samples are taken from the tail using EDTA coated capillary tubes (50 µL each time point). At time 0 (8:30 AM), a standard high fat meal (6 g butter, 6 g sunflower oil, 10 g nonfat dry milk, 10 g sucrose, 12 mL distilled water prepared fresh following Nb#6, JF, pg.1) is given by gavage (vol.=1% of body weight) to all animals.

Immediately following the high fat meal, 25 µg a LIGAND is injected i.p. in 100 µL saline. The same dose (25 µg/mL in 100 µL) is again injected at 45 min and at 1 hr 45 min. Control animals are injected with saline (3×100 µL). Untreated and treated animals are handled in an alternating mode.

Blood samples are taken in hourly intervals, and are immediately put on ice. Plasma is prepared by centrifugation following each time point. Plasma is kept at −20° C. and free fatty acids (FFA), triglycerides (TG) and glucose are determined within 24 hours using standard test kits (Sigma and Wako). Due to the limited amount of plasma available, glucose is determined in duplicate using pooled samples. For each time point, equal volumes of plasma from all 8 animals per treatment group are pooled.

Example 6

Effect of LIGAND on Plasma FFA, TG and Glucose in C57 BL/6 Mice

Briefly, 14 mice re fasted for 2 hours prior to the experiment after which a baseline blood sample is taken. All blood samples are taken from the tail using EDTA coated capillary tubes (50 µL each time point). At time 0 (9:00 AM), a standard high fat meal (see Example 6) is given by gavage (vol.=1% of body weight) to all animals. Immediately following the high fat meal, 4 mice are injected 25 µg of LIGAND i.p. in 100 µL saline. The same dose (25 µg in 100 µL) is again injected at 45 min and at 1 hr 45 min. A second treatment group receives 3 times 50 µg LIGAND at the same intervals. Control animals are injected with saline (3×100 µL). Untreated and treated animals are handled in an alternating mode.

Blood samples are immediately put on ice. Plasma is prepared by centrifugation following each time point. Plasma is kept at −20° C. and free fatty acids (FFA), triglycerides (TG) and glucose are determined within 24 hours using standard test kits (Sigma and Wako).

Example 7

Effect of LIGAND on FFA Following Epinephrine Injection

In mice, plasma free fatty acids increase after intragastric administration of a high fat/sucrose test meal. These free fatty acids are mostly produced by the activity of lipolytic enzymes i.e. lipoprotein lipase (LPL) and hepatic lipase (HL). In this species, these enzymes are found in significant amounts both bound to endothelium and freely circulating in plasma. Another source of plasma free fatty acids is hormone sensitive lipase (HSL) that releases free fatty acids from adipose tissue after β-adrenergic stimulation. To test whether LIGAND also regulates the metabolism of free fatty acid released by HSL, mice are injected with epinephrine.

Two groups of mice are given epinephrine (5 µg) by intraperitoneal injection. A treated group is injected with a LIGAND (25 µg) one hour before and again together with epinephrine, while control animals receive saline. Plasma is isolated and free fatty acids and glucose are measured.

Example 8

Effect of LIGAND on FFA Following Intralipid Injection

Two groups of mice are intravenously (tail vein) injected with 30 µL bolus of Intralipid-20% (Clintec) to generate a sudden rise in plasma FFAs, thus by-passing intestinal absorption. Intralipid is an intravenous fat emulsion used in nutritional therapy). A treated group (LIGAND-treated) is injected with LIGAND (25 µg) at 30 and 60 minutes before Intralipid is given, while control animals receive saline. Plasma is isolated and FFAs are measured as described previously. The effect of LIGAND on the decay in plasma FFAs following the peak induced by Intralipid injection is then monitored.

Example 9

Effect of LIGAND on Weight Gain and Weight Loss of Mice and on Maintenance of Weight Loss in Mice In the first experiment, 10-week-old male C57BL/6J mice are put on a very high fat/sucrose purified diet for 19 days to promote weight gain; the average body weight at this time is 30 g. The mice are then surgically implanted with an osmotic pump (Alzet, Newark Del.) delivering either 2.5 µg/day of LIGAND or physiological saline. The mice are continued on the high fat diet and their body weight was recorded over the following 10-day period.

Weight gain by mice treated with saline in contradistinction to weight loss by mice treated with LIGAND is taken as evidence that in this inbred strain of normal mice, a continuous infusion of a daily low dose of LIGAND can prevent weight gain caused by high fat/sucrose feeding, in a sustainable way.

Data are expressed throughout as mean±SEM; a p-value<0.05 is considered statistically significant. Statistical analysis is typically done using either the unpaired Student's t test or the paired Student's t test.

Maintenance of Weight Loss in Mice

In order to demonstrate the ability of LIGAND to maintain weight loss, normal mice are put on a reduced calorie diet to promote weight loss. The reduced calorie diet is continued until the mice lose 10% of their initial weight. A second group of mice are continued on the reduced calorie diet until the mice lose 20% of their initial weight. The mice are then surgically implanted with an osmotic pump (Alzet, Newark, Del.) delivering either 2.5 µg/day of LIGAND or physiological saline. The mice are returned to a normal diet and their body weights are recorded over a 10-day period. After 10 days, the outcome wherein mice treated with LIGAND have a lower weight than mice treated with saline is taken to provide evidence that treatment with LIGAND promotes the maintenance of weight loss.

Example 10

Assessment of Homotrimer Formation by gAPM1, gC2P, gZADJ-2 or gZADJ-7 Polypeptide Fragment.

Homotrimer formation by gAPM1, gC2P, gZADJ-2 or gZADJ-7 polypeptide fragment is assessed using sedimentation equilibrium in analytical centrifuges, a method that determines molecular weight accurately and independently of other physical factors such as shape.

Candidate gAPM1, gC2P, gZADJ-2 or gZADJ-7 polypeptide fragment homotrimer is purified, for example using a protocol comprising a method of gel filtration such as 16/60 superdex 200 gel filtration column (Amersham). Said purified candidate gAPM1, gC2P, gZADJ-2 or gZADJ-7 polypeptide fragment homotrimer protein concentration is made 3 µM in 5.7 mM phosphate (pH 7.5), 137 mM NaCl, 2.7 mM KCl. Samples are centrifuged at 8,000 rpm for 18 hours at 10° C. in a Beckman XL-A analytical ultracentrifuge before absorbance is recorded. The data are fit globally, using MacNonlin PPC [Johnson ML et al., Biophys J (1981) 36:575-8; Schuster TM et al., Curr Opin Struct Biol (1996) 6:650-8; Hensley P, Structure (1996) 4:367-73; the disclosures of which are incorporated herein by reference in their entirety] to the following equation that describes the sedimentation of a homogeneous species: $Abs=B+A'exp[H \times M (x^2-x_0^2)]$ where Abs=absorbance at radius x, A'=absorbance at reference radius $x_0$, $H=(1-\upsilon\rho)\omega^2/2RT$, R=gas constant, T=temperature in Kelvin, $\upsilon$=partial specific volume=0.71896131 mL/g, $\rho$=density of solvent=1.0061 g/ml, $\omega$=angular velocity in radians/s, M=apparent molecular weight, and B=solvent absorbance (blank).

TABLE 1

Amino Acid Residues Comprising the Structural Domains of PROLIXIN SEQ ID NO: 2 Description

| EC DOMAIN | TRANSMEMBRANE DOMAIN | IC DOMAIN |
|---|---|---|
| 1-76 | 77-99 | 100-184 |

EC, extracellular domain; IC, intracellular domain

TABLE 2

APM1, C2P, ZADJ-2 and ZADJ-7

>APM1 polypeptide sequence:

MLLLGAVLLLLALPGHDQETTTQGPGVLLPLPKGACTGWMAGIPGHPGHNGAPGRDGRD

GTPGEKGEKGDPGLIGPKGDIGETGVPGAEGPRGFPGIQGRKGEPGEGAYVYR<u>SAFSVGLET</u>

<u>YVTIPNMPIRFTKIFYNQQNHYDGSTGKFHCNIPGLYYFAYHITVYMKDVKVSLFKKDKAM</u>

<u>LFTYDQYQENNVDQASGSVLLHLEVGDQVWLQVYGEGERNDNDSTFTGFLLYH</u>

<u>DTN</u> (244) (SEQ ID NO: 3)

>C2P polypeptide sequence:

MRIWWLLLAIEICTGNINSQDTCRQGHPGIPGNPGHNGLPGRDGRDGAKGDKGDAGEPG

RPGSPGKDGTSGEKGERGADGKVEAKGIKGDQGSRGSPGKHGPKGLAGPMGEKGLRGETG

PQGQKGNKGDVGPTGPEGPRGNIGPLGPTGLPGPMGPIGKPGPKGEAGPTGPQGEPGVRGIR

GWKGDRGEKGKIGETLVLPK<u>SAFTVGLTVLSKFPSSDMPIKFDKILYNEFNHYDTAAGKFTC</u>

TABLE 2-continued

APM1, C2P, ZADJ-2 and ZADJ-7

HIAGVYYFTYHITVFSRNVQVSLVKNGVKILHTKDAYMSSEDQASGGIVLQLKLGDEVWLQ

VTGGERFNGLFADEDDDTTFTGFLLFSSP (333)
(SEQ ID NO: 4)

>ZADJ-2 polypeptide sequence:

MIPWVLLACALPCAADPLLGAFARRDFRKGSQLVCSLPGPQGPPGPPGAPGPSGMMGRM

GFPGKDGQDGHDGDRGDSGEEGPPGRTGNRGKPGPKGKAGAIGRAGPRGPKGVNGTPGK

HGTPGKKGPKGKKGEPGLPGPCSCGSGHTKSAFSVAVTKSYPRERLPIKFDKILMNEGGHY

NASSGKFVCGVPGIYYFTYDITLANKHLAIGLVHNGQYRIRTFDANTGNHDVASGSTILALK

QGDEVWLQIFYSEQNGLFYDPYWTDSLFTGFLIYADQDDPNEV (285)
(SEQ ID NO: 5)

>ZADJ-7 polypeptide sequence:

MGKEDTQETRTEPKMFVLLYVTSFAICASGQPRGNQLKGENYSPRYICSIPGLPGPPGPPG

ANGSPGPHGRIGLPGRDGRDGRKGEKGEKGTAGLRGKTGPLGLAGEKGDQGETGKKGPIG

PEGEKGEVGPIGPPGPKGDRGEQGDPGLPGVCRCGSIVLKSAFSVGITTSYPEERLPIIFNKVL

FNEGEHYNPATGKFICAFPGIYYFSYDITLANKHLAIGLVHNGQYRIKTFDANTGNHDVASG

STVIYLQPEDEVWLEIFFTDQNGLFSDPGWADLFSGFLLYVDTDYLDSISEDDEL (303)
(SEQ ID NO: 6)

What is claimed is:

1. A method of screening a candidate compound for binding with a PROLIXIN polypeptide comprising:
    a) providing a PROLIXIN polypeptide comprising amino acids 1 to 76 of SEQ ID NO: 2;
    b) obtaining a candidate compound that is to be screened for its ability to interact with the PROLIXIN polypeptide, said candidate compound comprising a self-assembling homotrimeric polypeptide selected from a APM1, gC2P, gZAJD-2 or gZAJD-7;
    c) bringing into contact said PROLIXIN polypeptide and said candidate compound;
    d) detecting complexes formed between said polypeptide and said candidate compound; and
    e) identifying candidate compounds that bind to said PROLIXIN polypeptide.

2. The method according to claim 1, wherein said self-assembling homotrimeric polypeptide is gAPM1 (SEQ ID NO: 3).

3. The method according to claim 1, wherein said self-assembling homotrimeric polypeptide is gC2P (SEQ ID NO: 4).

4. The method according to claim 1, wherein said self-assembling homotrimeric polypeptide is gZAJD-2 (SEQ ID NO: 5).

5. The method according to claim 1, wherein said self-assembling homotrimeric polypeptide is gZAJD-7 (SEQ ID NO: 6).

* * * * *